United States Patent [19]

Guardino et al.

[11] Patent Number: 4,525,453
[45] Date of Patent: Jun. 25, 1985

[54] PROCESS FOR RAPIDLY DIFFERENTIATING BETWEEN GRAM-NEGATIVE AND GRAM-POSITIVE MICROORGANISMS

[75] Inventors: Robert F. Guardino, Rochester; Robert T. Belly, Webster, both of N.Y.

[73] Assignee: Eastman Kodak Company, Rochester, N.Y.

[21] Appl. No.: 436,877

[22] Filed: Oct. 26, 1982

[51] Int. Cl.$^3$ .................... C12Q 1/04; G01N 21/52
[52] U.S. Cl. ........................... 435/34; 436/63; 436/170; 436/172; 436/904; 422/56
[58] Field of Search ............... 435/4, 29, 34; 422/56, 422/57; 436/175, 169, 170, 63, 56, 904, 172

[56] References Cited

U.S. PATENT DOCUMENTS

| | | | |
|---|---|---|---|
| 3,415,718 | 12/1968 | Forkman et al. | 435/14 |
| 3,496,066 | 2/1970 | Berger et al. | 435/34 |
| 3,503,741 | 3/1970 | Wilson et al. | 435/375 |
| 3,974,208 | 8/1976 | Dudzinski et al. | 260/501.11 |
| 3,992,158 | 11/1976 | Przybylowicz et al. | 422/57 |
| 4,126,516 | 11/1978 | Messing et al. | 435/34 |
| 4,225,669 | 9/1980 | Melnick et al. | 435/29 |
| 4,258,001 | 3/1981 | Pierce et al. | 422/56 |

FOREIGN PATENT DOCUMENTS

| | | | |
|---|---|---|---|
| 0054689 | 6/1982 | European Pat. Off. | 436/904 |
| 51-106752 | of 0000 | Japan . | |
| 51-57880 | of 0000 | Japan . | |
| 2031457 | 4/1980 | United Kingdom . | |
| 610863 | of 0000 | U.S.S.R. . | |
| 469747 | of 0000 | U.S.S.R. . | |

OTHER PUBLICATIONS

Bartholomew, J. W., and Mittwer, T., "The Gram Stain," Bact. Rev., 16:1–29, 1952.
Chapman, G. H., "A Superior Culture Medium for the Enumeration and Differentiation of Coliforms," J. Bact., 53:504, 1947.
Pollard, A. L., "A Useful Selective Bactericidal Property of Tergitol-7", Science, 103:758–759, 1946.
Baker, J.; Harrison, R. W.; and Miller, B. F., "Action of Synthetic Detergents on the Metabolism of Bacteria," J. Exp. Med., 73:249–271, 1941.
Dakay et al., "The Effect of Synthetic Detergents on the Formazan Formation of Various Environmental Bacteria," Zentralblatt Bakt. Hyg. I Abt. Orig. B 174, pp. 121–124, (1981).
Pearse, "Histochemistry, Theoretical and Applied," vol. 2, Third Ed., pp. 880–883, (1972).
Difco Manual, 9th Edition, 1977, Difco Laboratories Inc., Detroit, Mich. 48201, pp. 175–176.
Encyclopedia of Surface-Active Agents, vol. II, J. P. Sisley, 1964, p. 473.

*Primary Examiner*—Sidney Marantz
*Assistant Examiner*—William J. Herald
*Attorney, Agent, or Firm*—J. Lanny Tucker

[57] ABSTRACT

A process for rapidly differentiating between gram-positive and gram-negative microorganisms by mixing an anionic surfactant to inhibit the reduction capability of the gram-positive microorganisms, an electron transfer agent and a compound capable of being reduced to a detectable species by both gram-positive and gram-negative microorganisms in the absence of an anionic surfactant.

18 Claims, No Drawings

PROCESS FOR RAPIDLY DIFFERENTIATING BETWEEN GRAM-NEGATIVE AND GRAM-POSITIVE MICROORGANISMS

CROSS-REFERENCE TO RELATED APPLICATION

The present application is related to U.S. Ser. No. 453,033 filed Dec. 27, 1982 entitled "Inhibition of Reduction Activities of Leukocytes," of Guardino and Belly.

BACKGROUND OF THE INVENTION

1. Field of the Invention

The present invention relates to biochemical procedures and, in particular, to a method for rapidly differentiating gram-positive and gram-negative microorganisms.

2. Description of Related Art

All microorganisms can be separated into one of two classes, either gram-positive or gram-negative, based on their gram-stain reaction. The gram reaction is, therefore, a key test in the identification of microorganisms. In addition, owing to general structural and biochemical differences between gram-positive and gram-negative microorganisms, a different spectrum of antibiotics is used to treat infections caused by one of these classes than is used to treat infections caused by the other. Knowledge of the gram reaction of an infecting organism is, therefore, important for immediate selection of an appropriate antibiotic.

Currently, the gram-stain is a four-step staining procedure performed on a glass slide containing dried heat-fixed biological material. The method as it is commonly used today is the Hucker modification of the original staining procedure developed in 1883 by Hans Christian Gram.

To perform a gram stain, the slide is first flooded with a primary stain, a basic dye such as crystal violet, followed by the addition of 2–3 drops of a sodium bicarbonate solution to provide the necessary alkaline conditions. Alternatively, the sodium bicarbonate may be added directly to the crystal violet solution. After one minute, the crystal violet is rinsed off with tap water and is followed by the addition of a mordant, an iodine-potassium iodide mixture, which complexes with the crystal violet. The iodine is left on the slide for one minute and then gently washed off with tap water.

Decolorization to remove excess dye and dye from gram-negative cells is accomplished by allowing either a mixture of acetone and alcohol or an aqueous alcohol solution to flow down the slide until the runoff is colorless. This step is critical and either over or under decolorization can cause false results.

After rinsing with water, a counterstain is applied for one minute. The slide is again rinsed with water, air dried or blotted dry with absorbent paper, and examined visually under an oil immersion lens. Gram-positive organisms will retain the primary stain, while gram-negative organisms will be stained with the counterstain. Bartholomew et al., "The Gram Stain", Bact. Rev., 16:1–29, 1952 is a comprehensive review article describing this procedure and its interpretation. In Table 1, on page 10, of this reference, it is pointed out that gram-positive cells are more susceptible to death or growth inhibition by anionic detergents in general and higher alkyl sulfates. However, as shown in Example 5 below, compounds effective in growth inhibition are not necessarily effective in selectively inhibiting dye reduction in the rapid assay described herein.

Owing to the number of steps involved and the importance of proper decolorization technique, which will vary with type and amount of material present on the slide, as well as the need for heat-fixing the specimen to the slide, the actual staining procedure is difficult to automate completely. Furthermore, the entire procedure, including preparation of the slide, staining and viewing is time consuming, especially when numerous samples are involved. A one-step determination of the gram reaction that could be completely automated would greatly expedite this procedure and would therefore find a useful position in clinical microbiology.

U.S. Pat. No. 4,225,669 describes a bacterial staining composition and methods for analysis of both gram-negative and gram-positive bacteria. The staining composition comprises a chelating agent and a basic dye, both of which are operative at a pH above 7.0. Bacteria thus stained and concentrated by filtration or centrifugation are readily visible and semi-quantitative analysis is accomplished by comparing the gradation of color developed with a calibrated standard.

Differentiation of gram-negative and gram-positive bacteria is accomplished by treating the stained bacteria with an organic acid wash having a pH of about 2.5 to 2.6, which completely decolorizes only the gram-positive bacteria and thereby differentiates them from the gram-negative bacteria.

Chapman, "A Superior Culture Medium for the Enumeration and Differentiation of Coliforms," J. Bact., 53:504, 1947, describes a culture medium containing a surfactant, Tergitol-7, which inhibits or limits growth of non-coliform bacteria.

Pollard, "A Useful Selective Bactericidal Property of Tergitol-7," Science, 103:758–759, 1946, discusses the selective growth inhibition of a heat resistant bacillus in a starch/tryptone/agar medium by Tergitol-7 at a final concentration of 1:20,000 (Tergitol-7:bacillus).

Baker et al., "Action of Synthetic Detergents on the Metabolism of Bacteria," J. Exp. Med., 73:249–271, 1941, correlates chemical structure and properties of synthetic detergents with their effects on bacterial metabolism as determined by respiratory techniques. These effects were evaluated based on oxygen uptake by the bacteria. Anionic detergents, e.g., Tergitol-7, inhibited gram-positive bacterial respiration maximally at an acid pH and at a concentration of 1:3,000. Anionic detergents inhibited only the metabolism of gram-positive microorganisms, whereas cationic detergents inhibited the metabolism of both gram-positive and gram-negative microorganisms to the same degree. Tergitol-7 inhibited one gram-negative microorganism, *Proteus vulgaris*. Baker et al. observe on page 261 of the reference that the anionic detergents have the capacity to differentiate sharply between gram-positive and gram-negative microorganisms. However, this observation was based solely on respirometric procedures and would in no way suggest to a person of ordinary skill in the art a means for protecting a reducible compound in the presence of a gram-positive microorganism or a practical and rapid method for gram separation. Furthermore, the method would be expected to be limited to reactions occurring under aerobic conditions.

Dakay et al., "The Effect of Synthetic Detergents on Formazan Formation of Various Environmental Bacteria", Zentralblatt Bakt. Hyg. I Abt. Orig. B 174, pages 121-4 (1981) studied the effect of five detergents on dehydrogenase activity of a few bacteria as an indicator of environmental pollution. Two gram-positive organisms and two strains of a single gram-negative organism were used. Triphenyl tetrazolium chloride was used as an indicator of dehydrogenase activity. The cationic surfactant tested was very inhibitory to dehydrogenase activity. Of the two anionic detergents tested, the inhibitory effect was most noticeable with *Streptococcus faecalis* (0.03-0.08%), with *Micrococcus Sp.* (another gram-positive organism) proving to be less sensitive. *E. coli* (a gram-negative organism was inhibited at much higher concentrations. Non-ionic surfactants had no inhibitory effects.

SUMMARY OF THE INVENTION

The present invention relates to a method for inhibiting the ability of viable gram-positive microorganisms to reduce various dyes and other substrates.

Thus, for example, in a bioconversion reaction where it might be necessary for a gram-positive microorganism to be in contact with a reducible substance, but where the reduction of the substance is not desired, the present invention provides a means of the prevention of such reduction.

In preferred embodiments, the present invention relates to a method and an element for differentiating between gram-positive and gram-negative microorganisms.

More particularly, the present invention relates to a method for substantially preventing the reduction of a compound in admixture with a gram-positive microorganism capable of reducing said compound comprising including in said admixture an anionic surfactant in an amount sufficient to inhibit the reduction capability of the gram-positive microorganisms.

In the preferred embodiments referred to above, the present invention relates to:

A. a method for differentiating between viable gram-positive and viable gram-negative microorganisms comprising intermingling (a) said microorganisms, (b) an anionic surfactant, (c) an electron transfer agent, and (d) a compound capable of being reduced to a detectable species, in the absence of any reduction-inhibiting materials, by both gram-positive and gram-negative microorganisms and then determining whether or not said compound is reduced by determining the presence or absence of the detectable species, B. an analytical element for differentiating between viable gram-positive and viable gram-negative microorganisms comprising a porous lamina having contained therein (a) a compound capable of being reduced to a detectable species, in the absence of any reduction-inhibiting materials, by both gram-positive and gram-negative microorganisms and (b) an amount of an anionic surfactant sufficient to selectively inhibit the reduction of the compound by gram-positive microorganisms, and C. a composition for differentiating between viable gram-positive and viable gram-negative microorganisms comprising (a) a compound capable of being reduced to a detectable species, in the absence of any reduction-inhibiting materials, by both gram-positive and gram-negative microorganisms and (b) an amount of an anionic surfactant sufficient to selectively inhibit the reduction of the compound by gram-positive microorganisms.

Thus, the present invention provides a rapid, simple, and cost-effective means for differentiating the gram type of viable microorganisms.

One advantage of the present invention is the elimination of a decolorization step (as in Hucker's modification of the gram stain) since only gram-negative microorganisms are able to form a detectable colored end product.

A second advantage is that only viable cells can be differentiated, whereas in known methods (Bartholomew et al. and U.S. Pat. No. 4,225,669, supra), both viable and non-viable cells are stained.

A third advantage is that the method of the present invention can be easily automated and incorporated into an identification system for microorganisms in either a wet or a dry test format.

Further, the method can be at least semiquantitative as, for example, in the determination of the relative amounts of gram-positive and gram-negative microorganisms in a mixed sample.

DESCRIPTION OF THE PREFERRED EMBODIMENTS

The surfactants useful in the method and elements of the present invention can be any anionic surfactants comprising a hydrophobic group having one or more alkyl groups or aryl groups or a combination thereof; a hydrophilic anionic group; and the necessary counterions for completion of an ionically stable salt group.

The alkyl and/or aryl groups of the hydrophobic group of the anionic surfactant can be interrupted with heteroatom groups, for example, ester (i.e.,

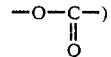

and/or ether groups, all having a combined total of from 6 to 20 carbon atoms, preferably from 10 to 17 carbon atoms. The carbon atoms of these alkyl and/or aryl groups can, optionally, have substituents attached thereto, such as aryl, alkyl, and halogen.

The identity of the hydrophilic anionic group and the anionic surfactants employed in the practice of this invention is not critical and any of the common groups known for this use can be employed, such as, for example, sulfate, sulfonate, phosphate, phosphonate, and carboxylate.

Similarly, the counterions used for completing the ionically stable salt group can be any of those commonly used and well known for this purpose such as, for example, the alkali metal and ammonium cations, including organic ammonium and amine-acid addition salt cations.

Exemplary aryl groups and aryl substituents include phenyl, naphthyl, biphenylyl, and the like. Exemplary alkyl groups and alkyl substituents include, for example, methyl, ethyl, propyl, isopropyl, butyl, amyl, hexyl, octyl, nonyl, decyl, dodecyl, and the like. Where halogen substituents are present, the fluoride is preferred, but others such as the chloride or the bromide may also be useful.

It will be understood by those skilled in the art that for each anionic surfactant useful in the method of the invention there will be an optimal concentration range and optimal environmental conditions for inhibiting the reductive capability of gram-positive microorganisms and for differentiation of gram-positive and gram-negative microorganisms. Further, there may be exceptions to the selective inhibitory action of anionic surfactants.

One such anomaly, described in the examples, infra, is the ability of dodecyl sodium sulfate to inhibit the ability of *Proteus vulgaris*, a gram-negative microorganism, to reduce [3-(4,5-dimethyl-2-thiazolyl)-2,5-diphenyl-2H-tetrazolium bromide] (MTT). As another example, it has been found that the anionic surfactant Triton X-200 exhibited substantially the same small inhibiting effect on both *E. coli* (gram-negative) and *S. aureus* (gram-positive) at the concentration tested. It is submitted, however, that the method disclosed herein for the inhibition of the reduction capability of gram-positive microorganisms and the differentiation of gram-positive and gram-negative microorganisms is one of general applicability and, given the present disclosure, a person skilled in the art will have no trouble applying the teaching thereof to specific cases. In particular, the skilled practitioner will realize that the efficacy of a previously untried anionic surfactant for this purpose can easily be tested using the procedure described in Example 1, infra.

Moreover, the preferred anionic surfactants, listed in Table I, appear to have a general utility in that, thus far, no gram-positive microorganisms have been found whose reducing power has not been inhibited in their presence, at the concentrations tested.

TABLE I

| Preferred Anionic Surfactants | | |
|---|---|---|
| Anionic Surfactants | Chemical Composition | Commercially Available From |
| Aerosol AY-100 | Diamyl ester of sodium sulfosuccinate | American Cyanamid Co. |
| Aerosol OT | Dioctyl ester of sodium sulfosuccinate | American Cyanamid Co. |
| Alkanol XC | Sodium alkyl (triisopropyl) naphthalene sulfonate | E. I. DuPont Co. |
| Bile Salts | A mixture of sodium cholate and sodium deoxycholate | Sigma Chemical Co. |
| Decyl Sodium Sulfate | — | — |
| Dodecyl Sodium Sulfate | — | — |
| FC-143 | $C_7$ fluorinated ammonium carboxylate | 3M Company |
| Gafac RS-610 | Free acid of a complex organic phosphate ester (Aliphatic $PO_4$ ester) | GAF Corp. |
| Hostapur SAS | Secondary alkane sulfonate Na salt | American Hoechst Corp. |
| Siponate DS-10 | Sodium dodecyl benzene sulfonate | Alcolac, Inc. |
| Sodium-1-dodecane Sulfonate | — | — |
| Tergitol 7 | Sodium-3,9-diethyl tridecanol sulfate derived from a secondary alcohol | Sigma Chemical Co. |
| Tetradecyl Sodium Sulfate | — | — |
| Ultrawet 60L | Organic salt (triethanolamine) of a linear alkylate sulfonate | Atlantic Richfield Co. |
| Witconate P10-59 | Amine salt of dodecyl benzene sulfonic acid | Witco Chemical Corp. |

Additional anionic surfactants useful in the practice of this invention can be found in any of several well-known references, such as Encyclopedia of Surfactants, Volumes 1-3, Michael and Irene Ash, Chemical Publishing Company, N.Y., 1980; McCutcheon's Emulsifiers & Detergents, North American Edition, McCutcheon Division, MC Publishing Company, Glen Rock, N.J., 1981; and Encyclopedia of Surface-Active Agents, J. P. Sisley, Chemical Publishing Company, N.Y., 1952.

The compound capable of being reduced to a detectable species, employed in the practice of this invention, can be any material that, in its oxidized form, is capable of being reduced by gram-positive and gram-negative microorganisms, in the absence of any reduction-inhibiting materials, to produce a detectable product. Such detection may, for example, be achieved by potentiometric means. Preferably, the detectable species will represent a material that is directly detectable by radiometric means. As used herein, the term "radiometric means" is defined to include any one of various analytical sensing means that employs radiation to provide an analytical result.

A partial listing of various detectable species that are directly detectable by radiometric means includes (a) colorimetrically detectable materials, such as colorants (i.e. dyes or pigments) that have extinction coefficients or absorption spectra that can be used to determine their presence or concentration using conventional colorimetric detection devices; and (b) radiation emissive materials, such as fluorescent materials, e.g. a fluorescent probe, that can be detected by a device capable of sensing radiation emitted from such materials.

The use of dyes or, preferably, dye precursors, as the detectable species is preferred. The use of a dye presents several possibilities: (1) the redox reaction may cause it to change from one color to another, (2) a colored dye may become colorless, or (3) a colorless material, i.e. a dye precursor, may become a colored dye. Alternative (3) is the one most preferred in the practice of this invention because the generation of color is generally more easily detectable than its disappearance.

Examples of dyes that can be used in the practice of this invention are methylene blue, dichloroindophenol, resazurin, and various tetrazolium compounds that, upon reduction, become colored formazan dyes, such as 3-(4,5-dimethyl-2-thiazolyl)-2,5-diphenyl-2H-tetrazolium bromide, 2,3,5-triphenyl-2H-tetrazolium chloride, tetranitro blue, tetrazolium chloride, and nitrotetrazolium violet. Tetrazolium salts are the preferred dye precursors for use in the present invention.

Tetrazolium salts useful in the present invention are those having general Formula I and that can be reduced by both gram-positive and gram-negative microorganisms to formazan dyes of general Formula II as follows:

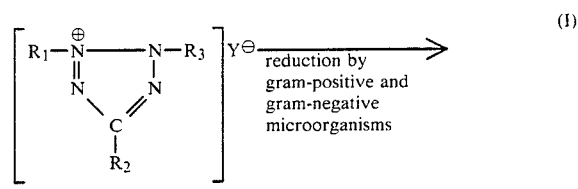

-continued

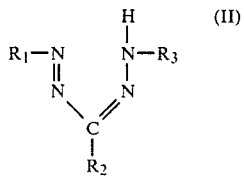

In the above Formulas I and II, $Y^\ominus$ represents an anion; $R_1$, $R_2$, and $R_3$ each represent an aryl or a heterocyclic substituent (preferably containing from 5 to 6 atoms, preferred hetero atoms being N, S, O, and Se), such as phenyl, substituted phenyl, naphthyl, substituted naphthyl, a substituted or unsubstituted thiazolyl, benzothiazolyl, oxazole, benzoxazole, selenazole, or benzoselenazole radical; $R_2$, in addition, can represent an alkyl group (e.g. methyl, butyl, hexyl, dodecyl, etc.) or a substituent (including acidic substituents) such as, for example, —H, —OH, —COOH, —$SO_3H$, —SH, —$NO_2$, etc., or any other substituent cited as being present in this position of the formazan or the tetrazolium salt in Chem. Rev., 55, 355–483 (1955); and the substituents $R_1$ and $R_3$ may contain an electron-sharing group capable of forming metal chelates or complexes. Examples of such chelating groups or complexes are primary, secondary, and tertiary amino, imino, substituted imino, oxime, thioether, keto, thioketo, hydroxyl, mercapto, carboxyl, sulfo, and phospho, alkoxy groups or complexes.

The tetrazolium salts useful in our invention also include bis-compounds of the general Formula III that can be reduced by gram-positive and gram-negative microorganisms to produce formazan of Formula IV:

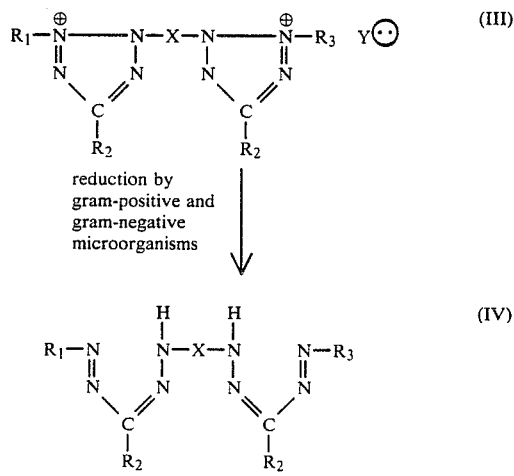

wherein $Y^\odot$ represents an anion and X an alkylene or arylene group; and $R_1$, $R_2$, and $R_3$, each represents a substituent as described above in connection with Formulae I and II.

Specific examples of tetrazolium salts that are useful in carrying out this invention are:

(a) triphenyl tetrazolium chloride (TTC);

(b) 2,2'-(p-diphenylene)-bis(3,5-diphenyl)tetrazolium chloride (also known as neotetrazolium chloride or NT);

(c) the methoxy derivative of NT (also known as BT blue tetrazolium);

(d) 2-(p-iodophenyl)-3-(p-nitrophenyl)-5-phenyl tetrazolium chloride (INT);

(e) 2,2'-di-p-nitrophenyl-5-5'-diphenyl-3-3'-(3,3'-dimethoxy-4,4'-biphenylene)ditetrazolium chloride (also known as nitro-BT);

(f) 2,2',5,5'-tetra-p-nitrophenyl-3,3'-(3,3'-dimethoxy-4,4'-biphenylene)-ditetrazolium chloride (also known as tetra-nitro BT or TNBT);

(g) 3-(4,5-dimethyl-thiazolyl-2)-2,5-diphenyl tetrazolium bromide (MTT);

(h) 2,2'-di-(3-nitrophenyl)-5,5'-dimethyl-3,3'-(4,4'-biphenylene)ditetrazolium chloride (also known as yellow tetrazolium or YT);

(i) 2,3,5-tri(p-nitrophenyl)-tetrazolium bromide (TNTTC);

(j) 2-phenyl-3-(3-methoxy-4-phenyl)-5-(p-nitrophenyl)-tetrazolium chloride (also known as half nitro BT); and (k) 2,5-di(p-nitrophenyl)-3-(3-methoxy-4-phenyl)-tetrazolium chloride (also known as half TNBT).

More detailed information about these compounds can be found in *Histochemistry, Theoretical and Applied*, by A. G. E. Pearse, Volume 2, Third Edition, pp. 880–883, Churchill Livingstone, Edinburgh and London, 1972.

The method for differentiating between gram-positive and gram-negative microorganisms can conveniently be carried out in conventional laboratory glassware, e.g. using test tubes or glass slides.

Alternatively, the anionic surfactant and detectable species can be incorporated into a porous lamina, i.e. a matrix of absorbent material, such as filter paper strips, by impregnation or otherwise, to yield test compositions suitable for differentiation of microorganisms present in a sample deposited thereon.

In addition, the method is used to particular advantage when carried out in an element having a porous lamina that is a spreading layer of the type described in U.S. Pat. Nos. 3,992,158 or 4,258,001. As described in these patents, such spreading layers can be self-supporting or can be supported by a strip or sheet of other material, such as a polyethylene terephthalate film. If desired, other layers serving other specialized purposes can also be present. Where more than one layer is present in such a device, it will often be beneficial to employ a "subbing" layer between two other layers to enhance adhesion between them.

The preferred general format of such elements can be depicted as follows:

| |
|---|
| Spreading/Reagent Layer |
| Subbing Layer |
| Support |

The element can, of course, have separate spreading and reagent layers as described in U.S. Pat. No. 3,992,158. In such a case, the anionic surfactant and reducible substance could both be in either the spreading layer or the reagent layer, or one could be in the spreading layer and one in the reagent layer. The primary criterion for choice in a given instance would be the necessity for the ability of the microorganism, the anionic surfactant, and the reducible substance to come together at the time of the analysis.

Dry test elements were prepared according to the above format and comprised the following:

A. a spreading/reagent layer comprising: bead polymers as described in U.S. Pat. No. 4,258,001, such as poly(vinyltoluene-co-p-t-butylstyrene-co-methacrylic acid), (preferred ratio, 66:33:1); binders, such as poly(n-butyl-acrylate-co-styrene-co-2-acrylamido-2-methyl-propane sulfonic acid) (preferred ratio 60:30:10); surfactants, such as Zonyl FSN; and, in addition, 1) electron transfer agents, such as phenazinemethosulfate, (2) chromogenic compounds, such as 3-(4,5-dimethyl-2-thiazolyl)-2,5-diphenyl-2H-tetrazolium bromide (MTT) and (3) any suitable anionic surfactant capable of inhibiting dye reduction by gram-positive bacteria, such as (1) Tergitol 7 and (2) Ultrawet 60L; and B. a subbing layer comprising (1) a binder, such as poly(acrylamide-co-N-vinyl-2-pyrrolidone) (90:10); and (2) a surfactant, such as Zonyl FSN; all coated, in the format described above, over C. a polyethylene terephthalate film support or other suitable material as described in U.S. Pat. No. 3,992,158.

In practicing the method of the present invention, the following procedures were carried out:

Microorganisms were maintained in brain heart infusion broth (BHI) and were grown to stationary phase overnight at 37° C. in BHI for use in solution studies.

Qualitative Determination of Microbial Dye Reduction-Solution Studies—Approximately 40 mL of overnight cultures of the organisms in BHI was centrifuged, decanted, and resuspended in 0.05M potassium phosphate buffer (KPB), pH 7.0. The optical density (OD) at 620 nm, as determined with a Bausch and Lomb Spectronic 20 spectrophotometer, of each cell suspension was adjusted with the above phosphate buffer so that a 1:30 dilution of the suspension resulted in an OD reading of 0.1. To 2.5 mL of cell suspension was added 2.5 mL of 0.05M KPB, pH 7.0, or 2.5 mL of the same buffer containing various concentrations of the inhibitor, 100 $\mu$L of 10% glucose as an energy source and 100 $\mu$L of phenazine methosulfate (PMS) (1 mg/mL methanol) (or any compound capable of transferring electrons from the microorganism to the reducible compound). The use of energy sources and/or electron transfer agents is preferred, but not necessarily required. The tubes were then mixed by vortex.

After mixing, 100 $\mu$L of [3-(4,5-dimethyl-2-thiazolyl)-2,5-diphenyl-2H-tetrazolium bromide] (MTT) (10 mg/mL methanol) (or any compound which forms a detectable end product upon microbial reduction) was added to each tube unless otherwise specified. Alternatively, a PMS solution of 3 mg/mL distilled water and a MTT solution of 5 mg/mL distilled water were used.

The tubes were mixed and visually examined immediately and at various time intervals during incubation at 37° C. The formation of a purple color was indicative of MTT reduction. The strength of reduction was graded as follows: 0 indicated no dye reduction seen; ± indicated faint reduction; 1+ indicated light reduction; 2+ indicated moderate reduction; 3+ indicated strong reduction; 4+ indicated very strong reduction.

The final cell concentrations used varied from $6 \times 10^8$ to $1 \times 10^9$ cells/mL depending on the organism tested unless otherwise specified.

Determination of Microbial Dye Reduction—Dry Element Mode—Cells were maintained and prepared as described above, except that the optical density was adjusted to 0.1 using a 1:20 dilution of the cell suspension. 10 $\mu$L of 0.05M KPB, pH 7.0, or 10 $\mu$L of cell suspension containing 0.2% glucose was spotted onto the dry element, which was incubated for 15 minutes at 37° C. in a moist chamber, unless otherwise specified. The reflectance density ($D_R$) of each spot was measured at 550 nm on a reflection densitometer without further incubation. The $D_R$ of the 0.5M KPB blank was either set to 0.00 or substracted from the test $D_R$, yielding a test $D_R$ corrected for background.

MATERIALS

Gram-negative microorganisms, including *Escherichia coli* (*E. coli*) ATCC 25922, *Klebsiella pneumonia* ATCC 13883, *Enterobacter cloacae* ATCC 23355, *Proteus vulgaris* ATCC 13315, *Serratia marcescens* ATCC 8100, and *Pseudomonas aeruginosa* ATCC 27853, and gram-positive microorganisms, including *Staphylococcus arueus* (*S. aureus*) ATCC 25923, *Staphylococcus epidermidis* ATCC 12228, *Streptococcus faecalis* ATCC 19433 and *Streptococcus pyogenes* ATCC 19615 were all obtained from American Type Culture Collection in Rockville, MD. Brain heart infusion broth was purchased from Difco Labs, Inc., Detroit, MI. Phenazine methosulfate, bile salts, Tergitol 7, Ultrawet 60L, polymyxin B, and tetracycline were purchased from Sigma Chemical Co., St. Louis, MO. Cetyl sodium sulfate, cetyl sodium sulfonate, octadecyl sodium sulfate, and eicosyl sodium sulfate were purchased from Research Plus Labs, Inc., Bayonne, NJ. Sodium-1-dodecane sulfonate was obtained from Regis Chemical Co., Morton Grove, IL. Hostapur SAS was purchased from American Hoechst Corp., Somerville, NJ, and FC 143 was acquired from 3M Co., St. Paul, MN. Zonyl FSN and Alkanol XC were purchased from E. I. DuPont Co., Wilmington, DE, and Witconate P10-59 was obtained from Witco Chemical Corp., New York, NY. Siponate DS-10 was received from Alcolac Inc., Baltimore, MD, and Aerosol OT and AY-100 were obtained frotm American Cyanamid Co., Wayne, NJ. Gafac RS-610 and Alipal CO-436 were purchased from GAF Corp., New York, NY, and subtilin was acquired from K/K Laboratories, Inc., Planinview, NY. Nitrotetrazolium violet and tetranitroblue tetrazolium chloride were purchased from Polysciences Inc., Warrington, PA.

All other chemicals were reagent grade and obtained from Eastman Kodak Company, Rochester, NY.

EXAMPLE 1

Selective Inhibition of Bacterial Reduction by Anionic Surfactants—Solution Mode A variety of salts and anionic surfactants, listed in Table II below, was examined as inhibitors of bacterial reduction of 3-(4,5-dimethyl-2-thiazolyl)-2,5-diphenyl-2H-tetrazolium bromide (MTT). Solution assays were performed, as described above, with *Staphylococcus aureus* (*S. aureus*, gram-positive) and *Escherichia coli* (*E. coli*, gram-negative) at approximate concentrations of $10^9$ cells/mL. The solutions were mixed, as described above, and incubated at 37° C. for 30 minutes.

TABLE II

| Effect of Various Anionic Surfactants on MTT Reduction by Gram-Positive and Gram-Negative Bacteria in Solution | | | |
|---|---|---|---|
| Anionic Surfactants | Inhibitor Concentration | (gram−) *E. coli* | (gram+) *S. Aureus* |
| Aerosol AY-100 | 1.0 g % | 4+ | 0 |
| Aerosol OT | 0.1 g % | 4+ | 0 to ± |
| Alkanol XC | 1.0 g % | 4+ | 0 |
| Bile Salts | 1.0 g % | 4+ | 0 |
| Decyl Sodium Sulfate | 1.0 g % | 3+ | 0 |

TABLE II-continued

Effect of Various Anionic Surfactants on MTT Reduction by Gram-Positive and Gram-Negative Bacteria in Solution

| Anionic Surfactants | Inhibitor Concentration | (gram−) E. coli | (gram+) S. Aureus |
|---|---|---|---|
| Dodecyl Sodium Sulfate | 0.1 g % | 4+ | 0 to ± |
| FC-143 | 1.0 g % | 3+ | 0 |
| Gafac RS-610 | 2.5% (v/v) | 3+ | 0 |
| Hostapur SAS | 1.0 g % | 4+ | 0 |
| Octyl Sodium Sulfate | 1.0 g % | 4+ | 1+ |
| Siponate DS-10 | 0.1 g % | 4+ | 0 |
| Sodium-1-dodecane Sulfonate | 1.0 g % | 4+ | 0 |
| Tergitol 7 | 0.1% (v/v) | 4+ | 0 |
| Tetradecyl Sodium Sulfate | 1.0 g % | 4+ | 0 |
| Ultrawet 60L | 0.1% (v/v) | 4+ | 0 |
| Witconate P10-59 | 1.0 g % | 4+ | 0 |

As shown in Table II, the gram-negative organism *E. coli* consistently showed a strong reduction of MTT (3+ or 4+ reaction) in the presence of a variety of anionic surfactants. In contrast, the reduction of MTT by *S. aureus*, a gram-positive organism, was strongly inhibited in the presence of anionic surfactants (0–1+ reaction).

EXAMPLE 2

Selective Inhibition of Gram-Positive Bacterial Reduction of MTT Under Anaerobic Conditions—Solution Mode Selective inhibition of gram-positive bacterial MTT reduction mediated by Tergitol 7 was demonstrated under anaerobic conditions to show that the inhibition of bacterial dye reduction was not dependent on oxygen utilization (aerobic respiration).

One mL of *E. coli* or *S. aureus* cell suspensions containing $5 \times 10^7$ cells/mL 0.05M KPB, pH 7.5, 0.2% glucose and 0.20 mM PMS was placed into each of two 1.5 mL cuvettes. The cuvettes were sealed with rubber stoppers and purged with nitrogen for 5 min. to eliminate oxygen. Tergitol 7 (at a final concentration of 0.1%) was added to one cuvette containing each organism, the other served as a control. MTT was added to all cuvettes to achieve a final concentration of 0.24 mM. Aerobic samples and controls lacking cells were included. The O.D. @ 540 nm was measured on all cuvettes for 10 min. on a Perkin Elmer model 572 spectrophotometer (sample chamber at 37° C.).

The change in absorbance in 10 min. was calculated and corrected for background by substracting the $\Delta O.D.$ in 10 min. values of appropriate controls lacking cells. The results are reported in Table III. The results obtained demonstrate selective inhibition of MTT reduction by the gram-positive bacterium, *S. aureus*, using Tergitol 7 in both aerobic and anaerobic environments. This indicates that the inhibition process is independent of oxygen utilization by the bacterial cells.

TABLE III

Selective Inhibition of MTT Reduction by Gram-Positive Bacteria (*S. aureus*) under Aerobic and Anaerobic Conditions

| Bacteria | Tergitol 7 | $\Delta O.D._{10}$ min. Aerobic | $\Delta O.D._{10}$ min. Anaerobic |
|---|---|---|---|
| *E. coli* (Gram-Neg.) | — | 0.37 | 0.44 |
| *E. coli* | 0.1% | 0.52 | 0.47 |
| *S. aureus* (Gram-Pos.) | — | 0.21 | 0.11 |
| *S. aureus* | 0.1% | 0.00 | 0.00 |

Example 3: Effect of Surfactant Charge on

TABLE III-continued

Selective Inhibition of MTT Reduction by Gram-Positive Bacteria (*S. aureus*) under Aerobic and Anaerobic Conditions

| Bacteria | Tergitol 7 | $\Delta O.D._{10}$ min. Aerobic | $\Delta O.D._{10}$ min. Anaerobic |
|---|---|---|---|

Inhibition of MTT Reduction - Solution Mode

Solution assays were carried out, as described in Example 1, substituting the various surfactants listed in Table IV below to determine the effect of surfactant charge on the inhibition of gram-positive bacterial dye reduction. The results shown in Table IV demonstrate that the anionic surfactants act as selective inhibitors of gram-positive bacterial dye reduction, resulting in distinct differentiation from gram-negative bacteria. In contrast, the cationic and nonionic surfactants tested failed to differentiate between gram-positive and gram-negative organisms.

TABLE IV

| Inhibitor | Concentration | Charge | (gram−) E. coli | (gram+) S. aureus |
|---|---|---|---|---|
| Tween-80 | 10% (v/v) | 0 | 3+ | 2+ |
| Dodecyl sodium sulfate | 0.1 g % | − | 4+ | 0 to ± |
| Tergitol 7 | 0.1% (v/v) | − | 4+ | 0 |
| Ultrawet-60L | 0.1% (v/v) | − | 4+ | 0 |
| Ethylhexadecyl dimethyl ammonium bromide | 1.0 g % | + | 1+ | 0 |

EXAMPLE 4

Selective Reduction Inhibition with Various Compounds—Solution Mode

Various compounds, listed in Table V below, were substituted for MTT and assays were carried out as described in Example 1, with the following exceptions: the inhibitor, Tergitol 7 (T7), was eliminated in one set of solutions for each bacterium (control solutions) and added at 0.1% in a second set of otherwise identical solutions. Also, the solutions were incubated for 60 min. at 37° C.

The results shown in Table V demonstrate that a wide variety of compounds can be substituted for MTT in the reaction.

TABLE V

| Dyes | *E. coli* (gram−) 0% T 7 | *E. coli* (gram−) 0.1% T 7 | *S. aureus* (gram+) 0% T 7 | *S. aureus* (gram+) 0.1% T 7 |
|---|---|---|---|---|
| 2,3,5-Triphenyl-2H—tetrazolium chloride | 4 | 2 | 4 | 0 |
| Tetranitro blue tetrazolium chloride | 4 | 4 | 4 | 0 |
| Nitrotetrazolium violet | 4 | 4 | 4 | 0 |
| Methylene blue | 3 | 3 | 3 | 0 |
| Dichloroindophenol | 4 | 4 | 4 | 0 |
| Resazurin | 2 | 3 | 2 | 0 |

EXAMPLE 5

Lack of Microbial Reduction Inhibition in the Presence of Known Bacterial Growth Inhibitors Compounds known to selectively inhibit the growth of bacteria, e.g., antibiotics, etc. were substituted for the anionic surfactant in solution assays, which were carried out, as described in Example 1, to determine whether these compounds would inhibit bacterial dye reduction.

Among the growth inhibitors tested were three antibiotics including subtilin, which is effective against gram-positive bacteria, polymyxin-B, which is effective against gram-negative bacteria, and tetracycline, which is effective against both gram types. These antibiotics are normally effective within a concentration range of 1-10 µg/mL. Concentrations of the antibiotics used were 20-1000 times greater than needed to inhibit bacterial growth. In addition, brilliant green and bovine oxgall, both of which inhibit gram-positive bacteria, phenethyl alcohol, which inhibits the growth of gram-negative bacteria, and potassium tellurite, which inhibits certain genera of both gram-positive and gram-negative bacteria were studied.

The results obtained are shown in Table VI.

TABLE VI
Effect of Known Antimicrobial Agents on MTT Reduction by E. coli and S. aureus

| Inhibitors | Inhibitor Concentration (g %) | (gram−) E. coli | (gram+) S. aureus |
| --- | --- | --- | --- |
| Brilliant green | .001 | 4+ | 4+ |
| Bovine oxgall | 4.0 | 4+ | 4+ |
| Phenethyl alcohol | 1.0 | 4+ | 4+ |
| Potassium tellurite (K₂TeO₃) | 10.0 | 4+ | 3+ |
| Subtilin | 0.02 | 4+ | 4+ |
| Polymyxin-B | 0.1 | 4+ | 4+ |
| Tetracycline | 0.1 | 4+ | 4+ |

The results shown in Table VI indicate that several known growth inhibitors of either gram-positive or gram-negative organisms fail to differentiate between the gram-positive test organism (S. aureus) and the gram-negative test organism (E. coli) based on rapid dye reduction methodology. These findings confirm that compounds effective in growth inhibition are not necessarily effective in selectively inhibiting dye reduction.

EXAMPLE 6

Selective Inhibition of Other Bacteria Found in Urinary Tract Infections—Solution Mode Solution assays were carried out as described in Example 1 to demonstrate selective inhibition of other genera of bacteria that may cause unitary tract infections. The organisms and inhibitors tested are listed in Tables VII and VIII, along with the results.

The results indicate that, in the method of the present invention, the anionic surfactants, from Example 1, are selective inhibitors against reduction by the gram-positive bacteria, but not by the gram-negative bacteria. One exception, the reduction of MTT by Proteus vulgaris, a gram-negative microorganism, was inhibited by dodecyl sodium sulfate.

TABLE VII

| | Inhibitors | | |
| --- | --- | --- | --- |
| | Dodecyl sodium sulfate (0.1 g %) | Tergitol 7 (0.1% v/v) | Ultrawet 60L (0.1% v/v) |
| Gram-positive: | | | |
| S. faecalis | ± | 0 | 0 |
| S. pyogenes | 0 | 0 | 0 |
| S. epidermidis | ± | 0 | 0 |
| Gram-negative: | | | |
| K. pneumoniae | 4+ | 4+ | 4+ |
| E. cloacae | 4+ | 4+ | 4+ |
| P. vulgaris | ±* | 4+ | 4+ |

TABLE VII-continued

| | Inhibitors | | |
| --- | --- | --- | --- |
| | Dodecyl sodium sulfate (0.1 g %) | Tergitol 7 (0.1% v/v) | Ultrawet 60L (0.1% v/v) |
| S. marcescens | 4+ | 4+ | 4+ |
| Ps. aeruginosa | 4+ | 4+ | 4+ |

*Cell lysis evident.

TABLE VIII

| Inhibitors | (g %) | (gram−) P. vulgaris | (gram+) S. faecalis |
| --- | --- | --- | --- |
| Alkanol XC | (0.25) | 4+ | ± |
| Witconate P10-59 | (5) | 4+ | 1+ |
| Siponate DS-10 | (0.5) | 4+* | 0 |
| Aerosol AY-100 | (1.0) | 4+ | ± |

*Cell lysis evident.

EXAMPLE 7

Concentration Effects of the Preferred Inhibitors—Solution Mode

Concentration effects of two preferred inhibitors, Tergitol 7 (0, 0.1, and 1.0%) and Ultrawet 60L (0.1 and 1.0%), on bacterial dye reduction by the organisms listed below in Table IX, were determined.

Solution assays were carried out as described in Example 1, incubating the solutions for 30 min. at 37° C.

The results shown in Table IX indicate that in the absence of surfactant both the gram-positive and the gram-negative bacteria tested reduced MTT to a similar extent. However, when the surfactants Tergitol 7 and Ultrawet 60L were added at either 0.1 or 1.0% (v/v), the reduction of MTT was inhibited with the gram-positive, but not the gram-negative, test organisms.

TABLE IX

| Organisms | Gram-Type | Control (no surfactant) 0% | Tergitol 7 | | Ultrawet 60L | |
| --- | --- | --- | --- | --- | --- | --- |
| | | | 0.1% | 1.0% | 0.1% | 1.0% |
| E. coli | − | 4+ | 4+ | 4+ | 4+ | 4+ |
| K. pneumoniae | − | 4+ | 4+ | 4+ | 4+ | 4+ |
| E. cloacae | − | 4+ | 4+ | 4+ | 4+ | 4+ |
| P. vulgaris | − | 4+ | 4+ | 4+ | 4+ | 4+ |
| S. marcescens | − | 3+ | 4+ | 4+ | 4+ | 4+ |
| Ps. aeruginosa | − | 4+ | 4+ | 4+ | 4+ | 4+ |
| S. aureus | + | 4+ | 0 | 0 | 0 | 0 |
| S. epidermidis | + | 4+ | 0 | 0 | 0 | 0 |
| S. faecalis | + | 4+ | 0 | 0 | 0 | 0 |
| S. pyogenes | + | 4+ | 0 | 0 | 0 | 0 |

EXAMPLE 8

Selective Inhibition of MTT Reduction by Tergitol 7—Dry Element Format

Selective inhibition by Tergitol 7 was demonstrated in a dry element format. Control Element I (no inhibitor) was compared with Test Element I (Tergitol 7 added as inhibitor).

Control Element I was prepared according to the general format described above: a polyethylene terephthalate film support was coated with a subbing layer comprising poly(acrylamide-co-N-vinyl-2-pyrrolidone) (90:10); and Zonyl FSN; and a spreading/reagent layer comprising beads of poly(vinyl toluene-co-p-t-butylstyrene-co-methacrylic acid) (66:33:1); poly(n-butyl acrylate-co-styrene-co-2-acrylamido-2-methylpropane sulfonic acid) (60:30:10), phenazinemethosulfate (0.011 g/m$^2$), 3-(4,5-dimethyl-2-thiazolyl)-2,5-diphenyl-2H-tetrazolium bromide (0.11 g/m$^2$), and Zonyl FSN.

Test Element I was coated in the same manner and comprised the same materials as Control Element I, except that Tergitol 7 (1.1 g/m$^2$) was added to the spreading/reagent layer composition.

The dry element assays were carried out as described above. The organisms used in the assays are listed in Table X. Results of these studies confirmed that Test Element I was effective in differentiating between the gram-positive and gram-negative bacteria tested.

TABLE X

| Organism | Gram Type | $D_R^b$ Control Element I | $D_R^b$ Test Element II |
|---|---|---|---|
| *Staphylococcus aureus* | + | 0.226$^c$ | 0.005$^c$ |
| *Staphylococcus epidermidis* | + | 0.194 | 0.003 |
| *Streptococcus faecalis* | + | 0.190 | 0.019 |
| *Streptococcus pyogenes* | + | 0.187 | −0.004 |
| *Escherichia coli* | − | 0.224$^c$ | 0.219$^c$ |
| *Klebsiella pneumoniae* | − | 0.182 | 0.211 |
| *Enterobacter cloacae* | − | 0.203 | 0.274 |
| *Proteus vulgaris* | − | 0.219 | 0.234 |
| *Serratia marcescens* | − | 0.178 | 0.225 |
| *Pseudomonas aeruginosa$^a$* | − | 0.130$^d$ | 0.049$^d$ |

$^a$Ten-minute incubation at 37° C.
$^b$The mean of 2 determinations unless specified below.
$^c$The mean of 3 determinations.
$^d$A single determination.

There was moderate inhibition of MTT reduction by *Ps. aeruginosa* with the coated element containing Tergitol 7. The reason for this exception in coated elements is unknown.

EXAMPLE 9

Comparison of the Effects of Tergitol 7 on *Proteus Vulgaris*—MTT Reduction (Present Invention) Vs. Respiration Tergitol 7, at a dilution of 1:3000 inhibited the respiration of *Proteus vulgaris*, a gram-negative bacteria, by 54–97% (See Baker et al., J. Exp. Med., 73:249–271, 1941). Data presented in the preceeding examples; Table IX—solution mode (Example 7) and Table X—dry element format (Example 8) demonstrate that at higher Tergitol 7 concentrations, i.e., 1:1000 (0.1%) and 1:100 (1.0%), the ability of *Proteus vulgaris* to reduce MTT is not inhibited.

This example points out the difference between the ability of Tergitol 7 to inhibit aerobic respiration of *P. vulgaris* (Baker et al., supra) and the failure of Tergitol 7 to inhibit the reductive ability of *P. vulgaris*.

The invention has been described in detail with particular reference to certain preferred embodiments thereof, but it will be understood that variations and modifications can be effected within the spirit and the scope of the invention.

What is claimed is:

1. A method for differentiating between viable gram-positive and viable gram-negative microorganisms comprising intermingling (a) gram-positive and gram-negative microorganisms, (b) an anionic surfactant in an amount sufficient to selectively inhibit the reduction capability of said gram-positive microorganisms, (c) an electron transfer agent, and (d) a compound capable of being reduced to a detectable species, in the absence of any reduction-inhibiting materials, by both gram-positive and gram-negative microorganisms and determining the presence or absence of the detectable species.

2. The method of claim 1 wherein the detectable species is a colorimetrically detectable material or a radiation emissive material.

3. The method of claim 2 wherein the colorimetrically detectable material is selected from the group consisting of methylene blue, dichloroindophenol, resazurin, and tetrazolium compounds that, upon reduction, become colored formazan dyes.

4. The method of claim 3 wherein the tetrazolium compound is 3-(4,5-dimethyl-2-thiazolyl)-2,5-diphenyl-2H-tetrazolium bromide.

5. The method of claim 4 wherein the anionic surfactant is sodium-3,9-diethyl tridecanol sulfate derived from a secondary alcohol.

6. The method of claim 1 wherein the anionic surfactant comprises a hydrophobic group hving one or more alkyl groups or aryl groups or a combination thereof; a hydrophilic anionic group; and the necessary counterion for completion of an ionically stable salt group.

7. An analytical element for differentiating between viable gram-positive and viable gram-negative microorganisms comprising a porous lamina having contained therein (a) a compound capable of being reduced to a detectable species, in the absence of any reduction-inhibiting materials, by both gram-positive and gram-negative microorganisms, (b) an electron transfer agent, and (c) an anionic surfactant in an amount sufficient to selectively inhibit the reduction of the compound by gram-positive microorganisms.

8. The element of claim 7 wherein the detectable species is a colorimetrically detectable material or a radiation emissive material.

9. The element of claim 8 wherein the colorimetrically detectable material is selected from the group consisting of methylene blue, dichloroindophenol, resazurin, and tetrazolium compounds that, upon reduction, become colored formazan dyes.

10. The element of claim 9 wherein the tetrazolium compound is 3-(4,5-dimethyl-2-thiazolyl)-2,5-diphenyl-2H-tetrazolium bromide.

11. The element of claim 10 wherein the anionic surfactant is sodium-3,9-diethyltridecanol sulfate derived from a secondary alcohol.

12. The element of claim 7 wherein the anionic surfactant comprises a hydrophobic group having one or more alkyl groups or aryl groups or a combination thereof; a hydrophilic anionic group; and the necessary counterion for completion of an ionically stable salt group.

13. A composition for differentiating between viable gram-positive and viable gram-negative microorganisms comprising (a) a compound capable of being reduced to a detectable species, in the absence of any reduction-inhibiting materials, by both gram-positive and gram-negative microorganisms, (b) an electron transfer agent, and (c) an anionic surfactant in an amount sufficient to selectively inhibit the reduction of the compound by gram-positive microorganisms.

14. The composition of claim 13 wherein the detectable species is a colorimetrically detectable material or a radiation emissive material.

15. The composition of claim 14 wherein the colorimetrically detectable material is selected from the group consisting of methylene blue, dichloroindophenol, resazurin, and tetrazolium compounds that, upon reduction, become colored formazan dyes.

16. The composition of claim 15 wherein the tetrazolium compound is 3-(4,5-dimethyl-2-thiazolyl)-2,5-diphenyl-2H-tetrazolium bromide.

17. The composition of claim 16 wherein the anionic surfactant is sodium-3,9-diethyltridecanol sulfate derived from a secondary alcohol.

18. The composition of claim 13 wherein the anionic surfactant comprises a hydrophobic group having one or more alkyl groups or aryl groups or a combination thereof; a hydrophilic anionic group; and the necessary counterion for completion of an ionically stable salt group.

* * * * *